United States Patent
Ikeda et al.

(10) Patent No.: US 6,903,212 B2
(45) Date of Patent: Jun. 7, 2005

(54) METHOD FOR REDUCING AN ORGANIC SOLVENT REMAINING IN β-FORM TRIS-(2,3,-EPOXYPROPYL)—ISOCYANURATE CRYSTALS

(75) Inventors: Hisao Ikeda, Funabashi (JP); Yasuhiro Gunji, Funabashi (JP); Motohiko Hidaka, Tokyoi (JP)

(73) Assignee: Nissan Chemical Industries, Ltd., Tokyo (JP)

( * ) Notice: Subject to any disclaimer, the term of this patent is extended or adjusted under 35 U.S.C. 154(b) by 0 days.

(21) Appl. No.: 09/973,766

(22) Filed: Oct. 11, 2001

(65) Prior Publication Data

US 2002/0045752 A1 Apr. 18, 2002

(30) Foreign Application Priority Data

Oct. 12, 2000 (JP) .......................................... 2000-311505

(51) Int. Cl.⁷ ............................................ C07D 251/30
(52) U.S. Cl. ....................................................... 544/221
(58) Field of Search .......................................... 544/221

(56) References Cited

U.S. PATENT DOCUMENTS

| 5,892,065 A | * | 4/1999 | Tsukamoto et al. ......... 549/515 |
| 6,124,454 A | * | 9/2000 | Ikeda et al. ................. 544/221 |

FOREIGN PATENT DOCUMENTS

| EP | 0 952 155 | 10/1999 |

\* cited by examiner

*Primary Examiner*—Venkataraman Balasubramanian
(74) *Attorney, Agent, or Firm*—Oblon, Spivak, McClelland, Maier & Neustadt, P.C.

(57) ABSTRACT

A process for producing β-form tris-(2,3-epoxypropyl)-isocyanurate crystals containing from 2 to 15 wt % of α-form tris-(2,3-epoxypropyl)-isocyanurate in the interior of the crystals, which comprises the following steps (A), (B), (C) and (D):

(A) a step of reacting cyanuric acid with epichlorohydrin to form an addition product of cyanuric acid and epichlorohydrin, followed by dehydrochlorination to obtain a reaction solution containing tris-(2,3-epoxypropyl)-isocyanurate, (B) a step of removing epichlorohydrin from the reaction solution containing tris-(2,3-epoxypropyl)-isocyanurate obtained in step (A), and dissolving the obtained tris-(2,3-epoxypropyl)-isocyanurate in a solvent, (C) a step of gradually cooling the liquid obtained in step (B) at a cooling rate within 20° C./hr for crystallization, followed by filtration to obtain crystals, and (D) a step of washing and drying the crystals obtained in step (C).

37 Claims, No Drawings

METHOD FOR REDUCING AN ORGANIC SOLVENT REMAINING IN β-FORM TRIS- (2, 3,-EPOXYPROPYL)— ISOCYANURATE CRYSTALS

BACKGROUND OF THE INVENTION

1. Field of the Invention

The present invention relates to β-form tris-(2,3-epoxypropyl)-isocyanurate crystals and a process for their production. Particularly, it relates to a process for producing such crystals efficiently as a product of high purity wherein the content of α-form tris-(2,3-epoxypropyl)-isocyanurate which is present on the surface of the crystals in a form to be extracted by an alcohol, is not more than 2 wt %, and epichlorohydrin and an organic solvent hazardous to human bodies or to applications to electronic materials, are reduced to a level of not more than 1,000 ppm.

2. Discussion of Background

In view of an increasing demand in recent years for the properties required for a solder resist material, such as adhesion, electrical insulating properties, soldering heat resistance and solvent resistance, a solder resist ink composition is presently used which is a combination of a photosensitive prepolymer and a thermosetting resin. Namely, it is designed to satisfy the above required properties by forming a solder resist pattern by the photosensitive prepolymer, followed by thermosetting. Further, demands have been increasing for high densification of printed circuit boards along with a trend for light weight and miniaturization of electronic appliances in recent years, for low bleeding during formation of solder resist patterns for surface mounting of parts and for precision in embedding between circuits. Accordingly, as the thermosetting resin to be incorporated to the solder resist ink, a fine particulate solid epoxy having high solvent resistance is desired.

As a solid epoxy to satisfy the above required properties, tris-(2,3-epoxypropyl)-isocyanurate may be mentioned. Tris-(2,3-epoxypropyl)-isocyanurate has three asymmetric carbon atoms, and crystals made of an equimolar mixture of (2R,2'R,2"R)-tris-(2,3-epoxypropyl)-isocyanurate and (2S,2'S,2"S)-tris-(2,3-epoxypropyl)-isocyanurate, wherein all of the three asymmetric carbon atoms are optically isotropic, are commonly called β-form crystals and known to give crystals having a high melting point of a level of about 150° C. This is attributable to the fact that a pair of these two types of enantiomers form a molecular lattice having firm six hydrogen bonds and thus form a crystal lattice. On the other hand, crystals made of a mixture of (2R,2R,2S)-tris-(2,3-epoxypropyl)-isocyanurate and (2S,2S,2R)-tris-(2,3-epoxypropyl)-isocyanurate, wherein one of the three asymmetric carbon atoms is different in the optical anisotropy, are commonly called α-form crystals, and they do not have the above crystal structure and accordingly present only a low melting point of a level of about 100° C. The β-form tris-(2,3-epoxypropyl)-isocyanurate crystals not only have a high melting point but also have a low solubility in various solvents. Accordingly, when they are used as a crosslinking agent for different types of compounds or for reactive polymers in the form of a one pack type reactive mixture, the reaction will not proceed during the storage, until they are forcibly cured. Such β-form crystals have been used for applications to electric and electronic materials, for example, as a solder resist ink composition of photocuring/thermosetting combined type.

The liquid epoxy composition is likely to undergo an increase in the viscosity during storage, since a part of the epoxy compound dissolves in the solvent, and entanglement with the photosensitive prepolymer is likely to result, whereby elution tends to be poor during washing off of the non-exposed portion. JP-B-7-17737 discloses use of β-form tris-(2,3-epoxypropyl)-isocyanurate as a hardly soluble epoxy compound. β-form tris-(2,3-epoxypropyl)-isocyanurate fine particles which have a high melting point and which are hardly soluble, are in a state enclosed by a photosensitive prepolymer, whereby they will not reduce the solubility of the photosensitive prepolymer at the non-exposed portion. Further, they are hardly soluble in an organic solvent, whereby the exposed portion is hardly eroded by a developer, whereby there will be no deterioration in the sensitivity. Further, the storage stability of the solder resist ink composition is excellent.

As a method for separating β-form tris-(2,3-epoxypropyl)-isocyanurate and α-form tris-(2,3-epoxypropyl)-isocyanurate from tris-(2,3-epoxypropyl)-isocyanurate, a separation method has been available wherein a solvent which dissolves α-form tris-(2,3-epoxypropyl)-isocyanurate relatively well and which hardly dissolves β-form tris-(2,3-epoxypropyl)-isocyanurate, for example, an alcohol such as methanol, is employed. For example, Journal of Thermal Analysis, vol.36 (1990) p.1819 discloses separation by means of a methanol solvent. Further, Plaste und Kautschuk 23 Jahrgang Heft 4/1975 discloses a method wherein firstly a methanol solvent is used for separating β-form tris-(2,3-epoxypropyl)-isocyanurate, and then the β-form tris-(2,3-epoxypropyl)-isocyanurate is purified by chloroform. Further, Kobunshi Ronbunshu (polymer report collection), vol.47, No.3 (1990) p.169, discloses a method wherein synthesized tris-(2,3-epoxypropyl)-isocyanurate is put into methanol, followed by heating and stirring, whereupon the non-dissolved content is collected by filtration, and the obtained non-dissolved substance is re-crystallized from methyl ethyl ketone to obtain β-form tris-(2,3-epoxypropyl)-isocyanurate crystals.

Many of β-form tris-(2,3-epoxypropyl)-isocyanurates obtained by such separation methods, hardly undergo crystal growth, and many of them have a small particle size, whereby the filtration operation in the filtration step tends to be very difficult. Accordingly, it is undesirable that the crystals obtained by recrystallization are too fine.

Further, by a single separation operation by the foregoing separation method, β-form tris-(2,3-epoxypropyl)-isocyanurate crystals tend to contain the solvent for recrystallization, chlorine-containing impurities or other impurities. Accordingly, it will be necessary to remove them by further carrying out recrystallization or by melting the crystals once. Particularly, if the remaining organic solvent is not adequately removed, when the tris-(2,3-epoxypropyl)-isocyanurate is used for e.g. a solder resist material, holes formed by evaporation of the solvent are likely to form on the surface of a printed circuit board, and original properties of the resist material can not be adequately obtained. Further, there may be a problem in an application in which surface smoothness is required. Further, in a case where the remaining organic solvent is a halogenated hydrocarbon, it is not suitable for applications to electronic materials. Further, in a case where the remaining organic solvent is a protic organic solvent, storage stability of a composition may be impaired by proton in some cases.

JP-B-48-24039 discloses a process wherein a chlorohydrin ester of isocyanuric acid obtained by reacting cyanuric acid with epichlorohydrin, is dehydrochlorinated with an alkali, the alkali metal chloride thereby formed is separated, and the obtained epichlorohydrin solution of tris-(2,3- epoxypropyl)-isocyanurate is concentrated to a tris-(2,3-epoxypropyl)-isocyanurate concentration of from 50 to 60%, and then the solution is cooled to from 20 to 25° C. to obtain tris-(2,3-epoxypropyl)-isocyanurate crystals in an yield of 27% based on cyanuric acid.

The tris-(2,3-epoxypropyl)-isocyanurate obtainable by a conventional process is known to contain α-form tris-(2,3-epoxypropyl)-isocyanurate and β-form tris-(2,3-epoxypropyl)-isocyanurate in a ratio of 3:1.

The yield of β-form tris-(2,3-epoxypropyl)-isocyanurate present at the reaction stage of JP-B-48-24039 is expected to be at most 20% based on cyanuric acid, and at the stage after the crystallization, the yield is expected to be at most 19% based on cyanuric acid. Whereas, the tris-(2,3-epoxypropyl)-isocyanurate crystals obtained in JP-B-48-24039 is 27% in yield based on cyanuric acid, from which the proportion of α-form tris-(2,3-epoxypropyl)-isocyanurate in the obtained crystals is calculated to be at least (27%−19%)/27%×100=30%. The results of a duplication test carried out by the present inventors also showed that the content of α-form tris-(2,3-epoxypropyl)-isocyanurate was at least 30%. It is considered that in the crystals obtained in JP-B-48-24039, a substantial amount of α-form tris-(2,3-epoxypropyl)-isocyanurate is attached on the surface of β-form tris-(2,3-epoxypropyl)-isocyanurate crystals or is present in the form of independent crystals.

Thus, the above process has a problem that the crystals contain a large amount of α-form tris-(2,3-epoxypropyl)-isocyanurate in the form to be extracted by an alcohol, and further a few thousands ppm of epichlorohydrin, etc. are contained in the interior of the crystals. Namely, as mentioned above, alcohol-soluble α-form tris-(2,3-epoxypropyl)-isocyanurate is present on the surface of the β-form tris-(2,3-epoxypropyl)-isocyanurate crystals or is independently present, whereby there is a problem that it dissolves in a solder resist composition to deteriorate the storage stability or to deteriorate the developability. Further, epichlorohydrin is composed of a hydrolyzable chlorine which is not only hazardous to human bodies but also hazardous to applications to electronic materials, and should be contained as little as possible.

Further, in a process to obtain tris-(2,3-epoxypropyl)-isocyanurate crystals by crystallization from a reaction solution using epichlorohydrin as a reaction solvent, there are following problems is safety in view of operation since a large amount of epichlorohydrin is handled as a solvent. Namely, an operator may be exposed to vapor of epichlorohydrin when seed crystals are charged in a dissolved state, and an operator may be exposed to vapor of epichlorohydrin during operation to repair clogging of a filter generated in a step of filtrating the crystals.

Further, hydrolyzable chlorine is required to be as little as possible in a field in which a high quality is required, however, epichlorohydrin tends to be contained in the interior of the crystals since crystallization is carried out from epichlorohydrin, and it is not easy to reduce epichlorohydrin to be not more than 100 ppm for example.

SUMMARY OF THE INVENTION

It is an object of the present invention is to provide a process to make the amount of organic solvents remaining in tris-(2,3-epoxypropyl)-isocyanurate crystals obtained by a recrystallization method, particularly β-form tris-(2,3-epoxypropyl)-isocyanurate crystals, extremely small.

In the first aspect, the present invention provides a process for producing β-form tris-(2,3-epoxypropyl)-isocyanurate crystals containing from 2 to 15 wt % of α-form tris-(2,3-epoxypropyl)-isocyanurate in the interior of the crystals, which comprises the following steps (A), (B), (C) and (D):

(A) a step of reacting cyanuric acid with epichlorohydrin to form an addition product of cyanuric acid and epichlorohydrin, followed by dehydrochlorination to obtain a reaction solution containing tris-(2,3-epoxypropyl)-isocyanurate, (B) a step of removing epichlorohydrin from the reaction solution containing tris-(2,3-epoxypropyl)-isocyanurate obtained in step (A), and dissolving the obtained tris-(2,3-epoxypropyl)-isocyanurate in a solvent, (C) a step of gradually cooling the liquid obtained in step (B) at a cooling rate within 20° C./hr for crystallization, followed by filtration to obtain crystals, and (D) a step of washing and drying the crystals obtained in step (C).

In the second aspect, the present invention provides a process for producing β-form tris-(2,3-epoxypropyl)-isocyanurate crystals containing from 2 to 15 wt % of α-form tris-(2,3-epoxypropyl)-isocyanurate in the interior of the crystals, which comprises the following steps (A), (B), (C') and (D):

(A) a step of reacting cyanuric acid with epichlorohydrin to form an addition product of cyanuric acid and epichlorohydrin, followed by dehydrochlorination to obtain a reaction solution containing tris-(2,3-epoxypropyl)-isocyanurate, (B) a step of removing epichlorohydrin from the reaction solution containing tris-(2,3-epoxypropyl)-isocyanurate obtained in step (A), and dissolving the obtained tris-(2,3-epoxypropyl)-isocyanurate in a solvent, (C') a step of adding seed crystals to the liquid obtained in step (B) at a temperature lower by from 5 to 20° C. than the temperature at which the liquid forms a saturated solution, and gradually cooling the liquid at a cooling rate within 20° C./hr for crystallization, followed by filtration to obtain crystals, and (D) a step of washing and drying the crystals obtained in step (C').

In the third aspect, the present invention provides the process according to the first or second aspect, wherein step (A) is a step of reacting (a) 1 mol of cyanuric acid, (b) from 5 to 180 mols of epichlorohydrin and (c) from 0.001 to 0.1 mol of at least one compound selected from the group consisting of a tertiary amine, a quaternary ammonium salt, a quaternary ammonium base, a tri-substituted phosphine and a quaternary phosphonium salt, as a catalyst, to obtain a reaction solution, adding from 2 to 6 mols of an alkali metal hydroxide or an alkali metal alcoholate to the reaction solution for dehydrochlorination, and then removing the resulting alkali metal salt to obtain a reaction solution containing tris-(2,3-epoxypropyl)-isocyanurate.

In the fourth aspect, the present invention provides the process according to any one of the first to third aspects, wherein the solvent in which tris-(2,3-epoxypropyl)-isocyanurate is dissolved in step (B) is acetonitrile, toluene, dichloroethane, dioxane or dimethylformamide.

In the fifth aspect, the present invention provides the process according to any one of the second to fourth aspects, wherein the step (C') is a step (C") of heating the liquid obtained in step (B) to a temperature of at least the temperature at which the liquid forms a saturated solution, thereafter cooling the liquid to a temperature lower by from 5 to 20° C. than the temperature at which the liquid forms a saturated solution, and adding seed crystals thereto, and then gradually cooling the liquid at a cooling rate within 20° C./hr for crystallization, followed by filtration to obtain crystals.

In the sixth aspect, the present invention provides the process according to any one of the second to fifth aspects, wherein the addition of seed crystals in step (C') and step (C") satisfies the following formulae (1) and (2):

$$1 \times 10^{10} \geq T \geq 1 \times 10^2 \qquad (1)$$

$$T = 1.4 \times 10^{12} (m/(M \times D^3)) \qquad (2)$$

wherein T is the number of seed crystals added per the weight of tris-(2,3-epoxypropyl)-isocyanurate in the reaction solution (number/g), m is the weight (g) of seed crystals added, D is the average particle size of seed crystals which is from 2 to 300 μm, and M is the weight (g) of tris-(2,3-epoxypropyl)-isocyanurate in the reaction solution.

In the seventh aspect, the present invention provides the process according to any one of the second to sixth aspects, wherein the seed crystals added in step (C') and step (C") is β-form tris-(2,3-epoxypropyl)-isocyanurate, or a mixture of β-form tris-(2,3-epoxypropyl)-isocyanurate and α-form tris-(2,3-epoxypropyl)-isocyanurate.

In the eighth aspect, the present invention provides the process according to any one of the first to seventh aspects, wherein ultrasonic waves are applied to the liquid in the process of gradually cooling the liquid in step (C), (C') and (C").

In the ninth aspect, the present invention provides the process according to any one of the first to eighth aspects, wherein the washing in step (D) is carried out by using a solvent capable of providing a solubility of at least 0.5 g/100 g at 20° C. to α-form tris-(2,3-epoxypropyl)-isocyanurate and a solubility of less than 0.5 g/100 g at 20° C. to β-form tris-(2,3-epoxypropyl)-isocyanurate, in an amount of from 0.5 to 10 times by weight relative to the β-form tris-(2,3-epoxypropyl)-isocyanurate crystals.

In the tenth aspect, the present invention provides the process according to any one of the first to ninth aspects, wherein the average particle size of the crystals obtained in step (C), (C') and (C") is from 20 to 500 μm, and the drying in step (D) is carried out under atmospheric pressure or under reduced pressure in a gas stream at a temperature of from 120 to 140° C.

In the eleventh aspect, the present invention provides the process according to any one of the first to ninth aspects, wherein the average particle size of the crystals obtained in step (C), (C') and (C") is from 10 to 20 μm, and the drying in step (D) is carried out under atmospheric pressure or under reduced pressure in a gas stream at a temperature of from 40 to 120° C.

DETAILED DESCRIPTION OF THE PREFERRED EMBODIMENTS

Now, the present invention will be described in detail with reference to the preferred embodiments.

In the present invention, the β-form tris-(2,3-epoxypropyl)-isocyanurate crystals containing from 2 to 15 wt % of α-form tris-(2,3-epoxypropyl)-isocyanurate in the interior of the crystals, are obtainable as having an average particle size of from 10 to 500 μm. The content of α-form tris-(2,3-epoxypropyl)-isocyanurate present in the interior of the β-form tris-(2,3-epoxypropyl)-isocyanurate crystals is from 2 to 15 wt %, preferably from 4 to 13 wt %, as a proportion of (α-form)/(α-form+β-form).

As a method for measuring the content of α-form tris-(2,3-epoxypropyl)-isocyanurate present independently or on the surface of the β-form tris-(2,3-epoxypropyl)-isocyanurate crystals of the present invention, a solvent extraction method is, for example, available. Since the β-form has a very small solubility in an organic solvent as compared with the α-form, the measurement can be carried out with high precision. As the organic solvent to be used here, an alcohol type solvent such as methanol or ethanol may, for example, be mentioned.

Further, as a method for measuring the ratio of the α-form and the β-form in the entire crystals, $^1$H-NMR, IR or a method by HPLC by means of an optical resolution column, is available. As the optical resolution column, an amylose or cellulose derivative may be used as the stationary phase, whereby resolution can efficiently be carried out, and the measurement can be carried out with high precision.

The α-form tris-(2,3-epoxypropyl)-isocyanurate contained in the β-form tris-(2,3-epoxypropyl)-isocyanurate crystals of the present invention is from 2 to 15 wt %, and the analytical method is not limited to the method disclosed in this application.

The α-form tris-(2,3-epoxypropyl)-isocyanurate contained in the interior of the β-form tris-(2,3-epoxypropyl)-isocyanurate crystals will not be extracted by an organic solvent such as methanol, and when formed into an epoxy resin composition, it will not elute from the β-form tris-(2,3-epoxypropyl)-isocyanurate crystals.

In the process for producing β-form tris-(2,3-epoxypropyl)-isocyanurate crystals of the present invention, step (A) is a step of reacting cyanuric acid with epichlorohydrin to form an addition product of cyanuric acid and epichlorohydrin, followed by dehydrochlorination to obtain a reaction solution containing tris-(2,3-epoxypropyl)-isocyanurate. More specifically, step (A) is a step of reacting (a) 1 mol of cyanuric acid, (b) from 5 to 180 mols of epichlorohydrin and (c) from 0.001 to 0.1 mol of at least one compound selected from the group consisting of a tertiary amine, a quaternary ammonium salt, a quaternary ammonium base, a tri-substituted phosphine and a quaternary phosphonium salt, as a catalyst, to obtain a reaction solution, adding from 2 to 6 mols of an alkali metal hydroxide or an alkali metal alcoholate to the reaction solution for dehydrochlorination, and then removing the resulting alkali metal salt to obtain a reaction solution containing tris-(2,3-epoxypropyl)-isocyanurate.

In step (A), the catalyst for addition of epichlorohydrin to cyanuric acid is not particularly limited, and it may, for example, be a tertiary amine, a quaternary ammonium salt, a quaternary ammonium base, a tri-substituted phosphine or a quaternary phosphonium salt. It is preferred to use from 0.001 to 0.1 mol of the catalyst per mol of cyanuric acid. As examples of the catalyst, the tertiary amine may, for example, be tripropylamine, tributylamine or N,N'-dimethylpiperazine. The quaternary ammonium salt may, for example, be tetramethylammonium halide, tetraethylammonium halide or tetrabutylammonium halide, wherein the halide may, for example, be chloride, bromide or iodide. The quaternary ammonium base may, for example, be tetramethylammonium hydroxide, or benzyltrimethylammonium hydroxide. The tri-substituted phosphine may, for example, be tripropylphosphine, tributylphosphine, triphenylphosphine or tritolylphosphine, and the quaternary phosphonium salt may, for example, be tetramethylphosphonium halide, tetrabutylphosphonium halide, methyltriphenylphosphonium halide or ethyltriphenylphosphonium halide, wherein the halide may, for example, be chloride, bromide or iodide. Among the above mentioned compounds, a quaternary ammonium salt or a quaternary phosphonium salt is particularly preferred since the reaction proceeds efficiently under a milder condition with no substantial side reaction. Particularly preferred is a quaternary ammonium salt, such as tetramethylammonium halide, tetraethylammonium halide or tetrabutylammonium halide, wherein the halide is chloride or bromide, whereby the side reactions can further be suppressed, and removal of the catalyst after the reaction can easily be made simply by washing with water.

Further, in step (A), by the subsequent dehydrochlorination, a reaction solution containing tris-(2, 3-epoxypropyl)-isocyanurate can be obtained. The reagent to be used for this dehydrochlorination reaction is not particularly limited, and it may, for example, be an alkali metal hydroxide or an alkali metal alcoholate. It is preferred to use an alkali metal hydroxide or an alkali metal alcoholate in an amount within a range of from 2 to 6 mols, preferably from 2.5 to 4 mols, per mol of cyanuric acid. As such an alkali metal hydroxide, sodium hydroxide, potassium hydroxide or lithium hydroxide may, for example, be mentioned, and as such an alkali metal alcoholate, sodium methylate, sodium ethylate, potassium methylate or potassium ethylate may, for example, be mentioned. The tris-(2, 3-epoxypropyl)-isocyanurate thus obtained, contains β-form tris-(2,3-epoxypropyl)-isocyanurate and α-form tris-(2,3-epoxypropyl)-isocyanurate in a weight ratio of 1:3.

Step (B) is a step of removing epichlorohydrin from the reaction solution containing tris-(2,3-epoxypropyl)-isocyanurate obtained in step (A), and dissolving the obtained tris-(2,3-epoxypropyl)-isocyanurate in a solvent.

The reaction solution obtained in step (A) can be purified by washing with an aqueous sodium dihydrogen phosphate solution or with water. By washing the reaction solution, an alkali metal halide, a remaining catalyst, a remaining alkali metal hydroxide and other impurities contained in the reaction solution transfer from the reaction solution to an aqueous layer which is in contact with the reaction solution, and a purified reaction solution can be obtained.

The purified reaction solution can be concentrated by evaporating epihalohydrin. Evaporation can easily be carried out by a method of using, for example, a conventional distillatory, a rotary evaporator, a flash evaporator or a falling-film evaporator. Preferably, a coating film of the reaction solution is formed by an applicator on the surface of a substrate heated to a temperature of from 100 to 165° C. in a thickness of from 30 to 500 micron, preferably from 100 to 450 micron. Then, by evaporating epichlorohydrin from this coating film under reduced pressure, preferably under a pressure of the evaporating component of at most 5 mmHg, the evaporating component concentration in the coating film can be decreased in a short period of time. Such a liquid film containing substantially no evaporating component, which has an epichlorohydrin concentration of at most 100 ppm, particularly at most 10 ppm, can also be obtained by a method of heating the coating film formed as it is to evaporate the evaporating component. As a more efficient method, a coating film of the reaction solution or a concentrated liquid thereof is formed in a thickness of from 30 to 500 micron, preferably from 100 to 450 micron, on the surface of a substrate, preferably on a vertical surface, with an adequate spread in longitudinal and lateral directions, so that the evaporating component concentration sequentially decreases from one end to the opposite end, preferably from the top to the bottom; the evaporating component is evaporated from the coating film under a reduced pressure of at most 5 mmHg, for example, under a pressure of the evaporating component of from 0.1 to 5 mmHg, at a temperature of from 100 to 165° C., preferably from 120 to 160° C.; and a small amount of the reaction solution or a concentrated liquid thereof is continuously supplied to the one end of the coating film, having the highest evaporating component concentration, and at the same time, while gradually moving evaporation from the coating film and the liquid which maintains the film thickness toward the opposite end, a liquid having a reduced evaporating component concentration is continuously recovered from the opposite end, whereby an evaporating component can efficiently be removed from the reaction solution or a concentrated liquid thereof.

The obtained tris-(2,3-epoxypropyl)-isocyanurate may be dissolved in a solvent such as acetonitrile, toluene, dioxane or dimethylformamide.

In step (B), the solid content concentration of the reaction solution containing tris-(2,3-epoxypropyl)-isocyanurate is adjusted to from 10 wt % to 80 wt %, preferably from 20 wt % to 70 wt %.

If this concentration is too low, the volume efficiency tends to be poor, and no adequate amount can be obtained in one treatment.

On the other hand, if this concentration is too high, the change in the solubility to the change in the temperature will be large, whereby rapid crystallization will take place, whereby it is likely to take in α-form tris-(2,3-epoxypropyl)-isocyanurate, such being undesirable.

Step (C) is a step of gradually cooling the liquid obtained in step (B) at a cooling rate within 20° C./hr for crystallization, followed by filtration to obtain crystals.

Further, as step (C'), a step of adding seed crystals to the liquid obtained in step (B) at a temperature lower by from 5 to 20° C. than the temperature at which the liquid forms a saturated solution, and gradually cooling the liquid at a cooling rate within 20° C./hr for crystallization, followed by filtration to obtain crystals, may also be selected.

The necessity for maintaining the cooling temperature range required for this crystallization is to let a proper amount of the α-form be selectively contained in the precipitated β-form crystals.

In step (C'), seed crystals are added to the liquid obtained in step (B) at a temperature lower by from 5 to 20° C. than the temperature at which this liquid forms a saturated solution. If crystallization is carried out without adding seed crystals, a supersaturated state will continue in a cooling step, and at a latter half of cooling, crystallization takes place all at once, which may cause deterioration of purity due to inclusion of a solvent for crystallization or impurities such as α-form tris-(2,3-epoxypropyl)-isocyanurate, and accordingly, it is required to decrease the cooling rate in a case where no seed crystals are added.

In step (C') and (C''), prior to the addition of seed crystals, the reaction solution may be heated to a temperature of at least the temperature for forming a saturated solution to adequately dissolve tris-(2,3-epoxypropyl)-isocyanurate in the reaction solution, and then it is gradually cooled to a temperature lower by from 5 to 20° C. than the temperature for forming a saturated solution, and then seed crystals may be added. By this method, the particle size of the obtained crystals will be uniform, such being desirable in view of the filtration properties, etc.

The addition of seed crystals in step (C') and (C") satisfies the following formulae (1) and (2):

$$1\times10^{10} \geq T \geq 1\times10^{2} \quad (1)$$

$$T=10^{12}m/(M(4/3)\pi(D/2)^3 d)=1.4\times10^{12}(m/(M\times D^3)) \quad (2)$$

wherein T is the number of seed crystals added per weight of tris-(2,3-epoxypropyl)-isocyanurate in the reaction solution (number/g), m is the weight (g) of seed crystals added, D is the average particle size of seed crystals which is from 2 to 300 μm, M is the weight (g) of tris-(2,3-epoxypropyl)-isocyanurate in the reaction solution, and d is the true specific gravity of tris-(2,3-epoxypropyl)-isocyanurate.

In step (C') and (C") of the present invention, crystal growth starts from the added seed crystals as nuclei. The crystal size of the resulting β-form tris-(2,3-epoxypropyl)-isocyanurate can be controlled by the number of seed crystals added per weight of tris-(2,3-epoxypropyl)-isocyanurate in the reaction solution (T: number/g) as defined by the above formulae (1) and (2). The number (T) of seed crystals determined by the amount of seed crystals and the average particle size, is preferably at least $10^2$ particles/g, per weight of tris-(2,3-epoxypropyl)-isocyanurate in the reaction solution, when seed crystals having an average particle size of from 2 to 300 μm are used. If the number of seed crystals is small, the average crystal size of the crystallized β-form tris-(2,3-epoxypropyl)-isocyanurate becomes large, and if the number (T) of seed crystals is large, β-form tris-(2,3-epoxypropyl)-isocyanurate crystals having a small average crystal size will be crystallized. Further, if the number (T) of seed crystals is too much beyond $1\times10^{10}$ particles per g, the average particle size of the crystallized β-form tris-(2,3-epoxypropyl)-isocyanurate will be less than 10 μm, such being undesirable. Especially when seed crystals having an average particle size exceeding 100 μm are employed, if the number (T) of seed crystals is large, the added weight tends to be too much, such being undesirable.

If step (C") is carried out without heating the reaction solution to a temperature of at least the temperature for forming a saturated solution, while maintaining it at a temperature lower by from 5 to 20° C. than the temperature for forming a saturated solution, fine crystals will be formed in the reaction solution at this temperature, and such crystals will also serve as seed crystals together with the subsequently added seed crystals, whereby it tends to be difficult to control the number (T) of seed crystals. Accordingly, it is preferred that the reaction solution is heated once to a temperature of at least the temperature for forming a saturated solution, then it is cooled to a temperature lower by from 5 to 20° C. than the temperature for forming a saturated solution, and then seed crystals are added.

As the seed crystals to be added in step (C') and (C"), β-form tris-(2,3-epoxypropyl)-isocyanurate, or a mixture of β-form tris-(2,3-epoxypropyl)-isocyanurate and α-form tris-(2,3-epoxypropyl)-isocyanurate, may be employed.

After adding the seed crystals in step (C') and (C"), it is preferred to carry out stirring at the temperature for the addition for from 0.5 to 1 hour.

Then, in step (C), (C') and (C"), the liquid is gradually cooled to a temperature at which α-form tris-(2,3-epoxypropyl)-isocyanurate maintains a supersaturated state. This cooling rate is at most 20° C./hr, preferably at most 10° C./hr. If the cooling is carried out rapidly, rapid crystal precipitation will take place, and the purity will decrease due to inclusion of impurities, such being undesirable.

The precipitated β-form tris-(2,3-epoxypropyl)-isocyanurate crystals will be separated by filtration such as suction filtration, filter press filtration or centrifugal filtration.

In step (D), the β-form tris-(2,3-epoxypropyl)-isocyanurate obtained by filtration, can be washed with various organic solvents, since it contains impurities, or α-form tris-(2,3-epoxypropyl)-isocyanurate. The organic solvents include, for example, methanol, ethanol, isopropyl alcohol, methyl ethyl ketone, acetonitrile, and dimethylformamide. Among them, an organic solvent having a low boiling point, in which the solubility of β-form tris-(2,3-epoxypropyl)-isocyanurate is less than 0.5 g/100 g at 20° C., and the solubility of α-form tris-(2,3-epoxypropyl)-isocyanurate is at least 0.5 g/100 g at 20° C., is preferred. As an organic solvent having such characteristics, methanol, ethanol or isopropyl alcohol may, for example, be mentioned.

The washing can be carried out at a temperature of from 5 to 50° C., preferably from 5 to 30° C. At a high temperature such as from 30 to 50° C., the solubility increases, and the amount of the solvent can be saved, but the operation has to be carried out at a temperature close to the boiling point or the flash point. A centrifugal filtration machine has a possible danger of inflammation due to static electricity, and a highly safe pressure filtration machine has a possible problem such that α-form tris-(2,3-epoxypropyl)-isocyanurate dissolved in the washing solvent is likely to recrystallize in the filter material or in the cake by the passage of pressurizing gas, whereby the filtration property tends to deteriorate. Further, there will be a restriction such that a preheating installation for the solvent and a temperature-keeping installation not to let α-form tris-(2,3-epoxypropyl)-isocyanurate reprecipitate from the recovered solvent, will be required. Further, at a temperature of 50° C. or higher, a special thermal filtration system will be required. On the other hand, at a temperature lower than 5° C., a large amount of the solvent will be required.

The amount for washing varies depending upon the temperature and the solvent, but it is usually from 0.5 to 10 times by weight, preferably from 1 to 6 times by weight, relative to the dry weight of the β-form tris-(2,3-epoxypropyl)-isocyanurate crystals. As the washing method, the β-form tris-(2,3-epoxypropyl)-isocyanurate obtained by filtration, may again be slurried, followed by filtration. Otherwise, the solvent may be supplied during filtration to carry out the washing.

In step (D), after the washing, drying can be carried out under atmospheric pressure or under reduced pressure in a gas stream at a temperature of from 120 to 140° C. The above reduced pressure may be various pressures so long as it is a pressure lower than atmospheric pressure, such as a pressure of from 5 to 20 Torr. Further, the drying time is from 2 to 24 hours.

The above temperature of from 120 to 140° C. is a temperature of at least the melting point of α-form tris-(2, 3-epoxypropyl)-isocyanurate and a temperature of at most the melting point of β-form tris-(2,3-epoxypropyl)-isocyanurate. When the drying is carried out at this temperature in a gas stream, in the β-form tris-(2,3-epoxypropyl)-isocyanurate crystals containing α-form tris-(2,3-epoxypropyl)-isocyanurate in the interior of the crystals, a part of the α-form tris-(2,3-epoxypropyl)-isocyanurate will be melted and liquefied. Through this liquid portion, a remaining organic solvent or epichlorohydrin as an impurity will be discharged from the crystals out of the crystals. With the β-form tris-(2,3-epoxypropyl)-isocyanurate crystals containing from 5 to 15 wt % of α-form tris-(2,3-epoxypropyl)-isocyanurate in the interior of the crystals, obtained through the drying step in step (D), the remaining solvent and epichlorohydrin can be reduced to a level of at most 1,000 ppm as remaining solvent and 100 ppm as remaining epichlorohydrin, respectively. The reduction of the amount of the solvent remaining in the product can be accomplished in such a manner that the α-form tris-(2,3-epoxypropyl)-isocyanurate contained in the interior of the crystals is melted at a drying temperature of from 120 to 140° C., preferably from 125 to 135° C., to form liquid pores in the interior of the crystals, and the solvent is discharged through these liquid pores out of the crystals. In order to reduce the remaining solvent, a proper amount of α-form tris-(2,3-epoxypropyl)-isocyanurate present in the interior of the crystals and a proper washing/drying method are considered to be required. Especially with crystals having an average particle size of from 20 to 500 μm, the amount of the remaining solvent can be substantially reduced as between before and after the drying at from 120 to 140° C. Accordingly, with crystals having an average particle size of from 20 to 500 μm, drying under atmospheric pressure or under reduced pressure in a gas stream at a temperature of from 120 to 140° C. is necessary.

If the content of the α-form tris-(2,3-epoxypropyl)-isocyanurate present in the interior of the crystals is less than 2 wt %, pores formed by melting of the α-form tris-(2,3-epoxypropyl)-isocyanurate in the interior of the crystals tend to be little, whereby the amount of the solvent remaining in the formed crystals tends to increase.

On the other hand, if the content of the α-form tris-(2,3-epoxypropyl)-isocyanurate present in the interior of the crystals exceeds 15 wt %, during the drying at from 120 to 140° C., α-form tris-(2,3-epoxypropyl)-isocyanurate tends to bleed out from the interior of the crystals and act as a binder of particles, thus leading to coagulation, such being undesirable. If coagulation of particles takes place, the drying efficiency tends to be poor, and discharge from the drier tends to be difficult, and pulverization will be required anew, such being undesirable.

When the content of the α-form tris-(2,3-epoxypropyl)-isocyanurate in the interior of the crystals is from 2 to 15 wt %, and the drying temperature is from 120 to 140° C., coagulation of crystals due to bleeding out of α-form tris-(2,3-epoxypropyl)-isocyanurate to the surface of the crystal particles will scarcely take place.

Further, α-form tris-(2,3-epoxypropyl)-isocyanurate which is present independently or on the surface of the crystals and which is in the form to be extracted by an alcohol, is preferably at most 2 wt %. If this value exceeds 2 wt %, the shape of crystals or the particle size distribution tends to be non-uniform, whereby the filtration property tends to deteriorate, or a coagulation of particles due to fusion during the drying tends to occur. Further, when made into a photosetting/thermosetting combined one pack type resist ink composition, it tends to melt in a solvent thus leading to viscosity increase during the storage, and entanglement with the photosensitive prepolymer is likely to occur, whereby when the non-exposed portion after exposure is washed off, the elution tends to be poor.

When the α-form tris-(2,3-epoxypropyl)-isocyanurate which is present independently or on the surface of the crystals and which is in the form to be extracted by an alcohol, exceeds 2 wt % to some extent, it may be possible to reduce the value to a level of not more than 2 wt % by additional washing with e.g. methanol. However, if this value is from 10 to 20 wt %, the amount of methanol for additional washing at 20° C. will be required to be from 20 to 40 times by weight, such being an extremely inefficient method when the working efficiency and recovery or disposal of methanol are taken into consideration. If washing is carried out with heated methanol, the amount of methanol can be saved, but a centrifugal separating machine can not be used, and a pressure filtration machine has to be used, whereby the α-form tris-(2,3-epoxypropyl)-isocyanurate dissolved in methanol is likely to reprecipitate in the filter material or in the cake by the passage of the pressurizing gas, and the filtration property tends to deteriorate, and there will be a restriction from the viewpoint of installation.

In the present invention, when vigorous stirring such as ultrasonic wave vibration is applied during the crystallization in step (C), (C') and (C''), crystals having an average particle size of from 10 μm to 50 μm, particularly from 10 μm to 20 μm, will be precipitated. When the average particle size of crystals obtained in step (C), (C') and (C'') is from 10 to 20 μm, re-dissolution of α-form tris-(2,3-epoxypropyl)-isocyanurate is likely to take place, and due to the large specific surface area of such crystals, the α-form tris-(2,3-epoxypropyl)-isocyanurate is readily removable by washing with an organic solvent in step (D). Accordingly, in the crystals obtained in step (D), the α-form tris-(2,3-epoxypropyl)-isocyanurate contained in the interior of the crystals will be as small as from 2 to 5 wt %. And, with such crystals, the remaining solvent can be reduced to a level of at most 400 ppm simply by carrying out the drying in a gas stream under atmospheric pressure or under reduced pressure at a temperature of not higher than the melting point of the α-form tris-(2,3-epoxypropyl)-isocyanurate, such as from 40 to 120° C. By this method, the drying method can be simplified, although this method may be inferior from the viewpoint of the remaining solvent as compared with the method of drying at a temperature of at least the melting point of the α-form tris-(2,3-epoxypropyl)-isocyanurate. However, with such crystals, the remaining solvent can be reduced to a level of at most 300 ppm by drying at a temperature of at least the melting point of the α-form tris-(2,3-epoxypropyl)-isocyanurate (from 120 to 140° C.) in a gas stream under atmospheric pressure or under reduced pressure.

Method for Quantitative Analysis of the α-form tris-(2,3-epoxypropyl)-isocyanurate in the Interior of Crystals (1) The α-form tris-(2,3-epoxypropyl)-isocyanurate which can be extracted by methanol, is determined in such a manner that to the sample (crystals), 10 times of methanol is added, followed by stirring at 20° C. for 20 minutes, whereupon tris-(2,3-epoxypropyl)-isocyanurate in methanol is quantitatively analyzed by HPLC (high performance liquid chromatography).

Under this condition, if a value of at least 10 wt % is obtained, the treating temperature is changed from 20° C. to 40° C., and the measurement is carried out in the same manner, and the value will be taken as the measured value.

The tris-(2,3-epoxypropyl)-isocyanurate extractable by methanol is the α-form tris-(2,3-epoxypropyl)-isocyanurate present on the surface of the crystals.

(2) In the method for measuring the ratio of the α-form and the β-form in the entire crystals, a commercially available optical resolution column CHIRALPAK AD (manufactured by Daicel Chemical Industries, Ltd. (0.46 cm in diameter×25 cm in length)) was used for HPLC, n-hexane/2-propanol (40/60 v/v) is used as an eluting solution, the elution is carried out under such conditions that the column temperature is 24° C., and the flow rate is 1.0 ml/min, the sample crystals are dissolved in acetonitrile and further diluted with an eluting solution, and then poured into HPLC for chromatoseparation, whereby the β-form tris-(2,3-epoxypropyl)-isocyanurate will elute 11.00 minutes and 16.80 minutes, and the α-form tris-(2,3-epoxypropyl)- isocyanurate will elute 12.87 minutes and 14.20 minutes. The ratio of the α-form and the β-form in the entire crystals was calculated by the ratio of the areas of the respective peaks.

The α-form tris-(2,3-epoxypropyl)-isocyanurate which can not be extracted by methanol, can be calculated by the above (2)-(1). This α-form tris-(2,3-epoxypropyl)-isocyanurate which can not be extracted by methanol is believed to be the α-form tris-(2,3-epoxypropyl)-isocyanurate present in the interior of the β-form crystals.

Method for Quantitative Analysis of Organic Solvent Remaining in the Crystals

The organic solvent remaining in the crystals is determined in such a manner that to the sample (the crystals), 20 times of an organic solvent other than the solvent to be analyzed, such as dimethylformamide or acetonitrile, is added and heated to 80° C. to dissolve the crystals therein, followed by quantitative analysis by gas chromatography.

Measurements of the Average Particle Size and the Particle Size Distribution

The measurements were carried out in a wet system using methanol as a dispersant by a laser diffraction light scattering particle size distribution measuring apparatus. As the average particle size, a volume standard median diameter D50 was used.

Now, the present invention will be described in further detail with reference to Examples. However, it should be understood that the present invention is by no means restricted to such specific Examples.

EXAMPLE 1

Step (A): Into a flask equipped with a stirrer, a thermometer, a continuously dropping apparatus and an apparatus to concentrate an azeotropic vapor of epichlorohydrin and water under reduced pressure and to return only epichlorohydrin to the reaction system, 774 g (6 mols) of cyanuric acid, 8,328 g (90 mols) of epichlorohydrin and 213 g of a tetramethylammonium chloride aqueous solution having a concentration of 15.5 wt %, were added and refluxed with stirring at from 89 to 120° C. for 5 hours to carry out the reaction. Then, the temperature of the reaction system was cooled to 50° C., and 1,536 g of a 50 wt % sodium hydroxide aqueous solution was added and reacted for 6 hours under a reduced pressure of from 100 to 60 Torr with stirring while maintaining the temperature at 50° C. for dehydrochlorination. Then, formed sodium chloride was dissolved by an addition of 3,600 g of water for washing, followed by liquid separation, and 1,200 g of a 5 wt % sodium dihydrogen phosphate aqueous solution was further added for washing, whereby sodium hydroxide used in an excess amount was neutralized, followed by washing with 4,800 g of water.

Step (B): To 1,600 g of tris-(2,3-epoxypropyl)-isocyanurate obtained by evaporating the reaction solution to dryness at 120° C. under 2 Torr, 1,600 g of acetonitrile was added.

Step (C"): The temperature was raised to 57° C. to completely dissolve the solid content, then the liquid was cooled to 50° C. over one hour, whereupon 11.2 g of β-form tris-(2,3-epoxypropyl)-isocyanurate having an average particle size of 45 μm was added as seed crystals (the number T of seed crystals was 1×10⁵ particles/g).

The liquid was stirred at 50° C. for 1 hour and then cooled to 14° C. over 4 hours to precipitate β-form tris-(2,3-epoxypropyl)-isocyanurate crystals, which were collected by filtration.

Step (D): The obtained crystals were washed with 600 g of methanol, followed by filtration.

The obtained cake was dried at 80° C. under a reduced pressure of 5 Torr for 4 hours to obtain β-form tris-(2,3-epoxypropyl)-isocyanurate crystals in a yield of 291 g. The obtained crystals had amounts of remaining acetonitrile and epichlorohydrin of 1,000 ppm and 40 ppm, respectively, an epoxy equivalent of 100 g/eq., an amount of hydrolyzable chlorine of 120 ppm, a content of α-form tris-(2,3-epoxypropyl)-isocyanurate extractable by methanol of 0.5 wt % and a content of α-form tris-(2,3-epoxypropyl)-isocyanurate not extractable by methanol contained in the interior of the crystals of 7.0 wt %. The crystals had a melting point of from 150 to 156° C., an average particle size of 80 μm, and they were white crystals. Further, the crystals were dried in a nitrogen stream at 130° C. under a reduced pressure of 10 Torr by a rotary evaporator for 24 hours to obtain β-form tris-(2,3-epoxypropyl)-isocyanurate crystals wherein the amounts of remaining acetonitrile and epichlorohydrin were 150 pm and 20 ppm, respectively.

EXAMPLE 2

Steps (A) to (C") were carried out in the same manner as in Example 1 except that seed crystals having an average particle size of 2.7 μm were used in step (C").

Step (D): The obtained crystals were washed with 600 g of methanol, followed by filtration.

The obtained cake was dried at 80° C. under a reduced pressure of 5 Torr for 4 hours to obtain β-form tris-(2,3-epoxypropyl)-isocyanurate crystals in a yield of 290 g. The obtained crystals had amounts of remaining acetonitrile and epichlorohydrin of 400 ppm and 20 ppm, respectively, an epoxy equivalent of 100 g/eq., an amount of hydrolyzable chlorine of 100 ppm, a content of α-form tris-(2,3-epoxypropyl)-isocyanurate extractable by methanol of 0.5 wt %, and a content of α-form tris-(2,3-epoxypropyl)-isocyanurate not extractable by methanol contained in the interior of the crystals of 4.0 wt %, and the crystals had a melting point of from 150 to 156° C. and an average particle size of 18 μm, and they were white crystals. Further, the crystals were dried in a nitrogen stream at 130° C. under a reduced pressure of 10 Torr by a rotary evaporator for 24 hours to obtain β-form tris-(2,3-epoxypropyl)-isocyanurate crystals wherein the amounts of remaining acetonitrile and epichlorohydrin were 200 ppm and 10 ppm, respectively.

EXAMPLE 3

Steps (A) to (C") were carried out in the same manner as in Example 1 except that the liquid was immediately cooled to 14° C. over 4 hours without carrying out stirring at 50° C. for 1 hour in step (C").

Step (D): The obtained crystals were washed with 600 g of methanol, followed by filtration.

The obtained cake was dried at 80° C. under a reduced pressure of 5 Torr for 4 hours to obtain β-tris-(2,3-epoxypropyl)-isocyanurate crystals in a yield of 290 g. The obtained crystals had amounts of remaining acetonitrile and epichlorohydrin of 1,400 ppm and 50 ppm, respectively, an epoxy equivalent of 101 g/eq., an amount of hydrolyzable chlorine of 150 ppm, a content of α-form tris-(2,3-epoxypropyl)-isocyanurate extractable by methanol of 0.5 wt %, and a content of α-form tris-(2,3-epoxypropyl)-isocyanurate not extractable by methanol contained in the interior of the crystals of 8.5 wt %, and the crystals had a melting point of from 149 to 155° C. and an average particle size of 75 μm, and they were white crystals. Further, the crystals were dried in a nitrogen stream at 130° C. under a reduced pressure of 10 Torr by a rotary evaporator for 24 hours to obtain β-form tris-(2,3-epoxypropyl)-isocyanurate crystals wherein the amounts of remaining acetonitrile and epichlorohydrin were 210 ppm and 30 ppm, respectively.

EXAMPLE 4

Step (A): Into a flask equipped with a stirrer, a thermometer, a continuously dropping apparatus and an apparatus to concentrate an azeotropic vapor of epichlorohydrin and water under reduced pressure and to return only epichlorohydrin to the reaction system, 774 g (6 mols) of cyanuric acid, 8,328 g (90 mols) of epichlorohydrin and 213 g of a tetramethylammonium chloride aqueous solution having a concentration of 15.5 wt %, were added and refluxed with stirring at from 89 to 120° C. for 5 hours to carry out the reaction. Then, the temperature of the reaction system was cooled to 50° C., and 1,536 g of a 50 wt % sodium hydroxide aqueous solution was added and reacted for 6 hours under a reduced pressure of from 100 to 60 Torr with stirring while maintaining the temperature at 50° C. for dehydrochlorination. Then, formed sodium chloride was dissolved by an addition of 3,600 g of water for washing, followed by liquid separation, and 1,200 g of a 5 wt % sodium dihydrogen phosphate aqueous solution was further added for washing, whereby sodium hydroxide used in an excess amount was neutralized, followed by washing with 4,800 g of water.

Step (B): To 1,600 g of tris-(2,3-epoxypropyl)-isocyanurate obtained by evaporating the reaction solution to dryness at 120° C. under 2 Torr, 6,400 g of toluene was added.

Step (C"): The temperature was raised to 110° C. to completely dissolve the solid content, then the liquid was cooled to 100° C. over one hour, whereupon 11.2 g of β-form tris-(2,3-epoxypropyl)-isocyanurate having an average particle size of 45 μm was added as seed crystals (the number T of seed crystals was 1×10$^5$ particles/g). The liquid was stirred at 100° C. for 1 hour and then cooled to 65° C. over 2 hours to precipitate β-form tris-(2,3-epoxypropyl)-isocyanurate crystals, which were collected by filtration.

Step (D): The obtained crystals were washed with 600 g of methanol, followed by filtration.

The obtained cake was dried at 80° C. under a reduced pressure of 5 Torr for 4 hours to obtain β-form tris-(2,3-epoxypropyl)-isocyanurate crystals in a yield of 294 g. The obtained crystals had amounts of remaining toluene and epichlorohydrin of 1,100 ppm and 40 pm, respectively, an epoxy equivalent of 100 g/eq., an amount of hydrolyzable chlorine of 210 ppm, a content of α-form tris-(2,3-epoxypropyl)-isocyanurate extractable by methanol of 0.5 wt % and a content of α-form tris-(2,3-epoxypropyl)-isocyanurate not extractable by methanol contained in the interior of the crystals of 7.0 wt %. The crystals had a melting point of from 150 to 156° C., an average particle size of 55 μm, and they were white crystals. Further, the crystals were dried in a nitrogen stream at 130° C. under a reduced pressure of 10 Torr by a rotary evaporator for 24 hours to obtain β-form tris-(2,3-epoxypropyl)-isocyanurate crystals wherein the amounts of remaining toluene and epichlorohydrin were 130 ppm and 20 ppm, respectively.

EXAMPLE 5

Step (A): Into a flask equipped with a stirrer, a thermometer, a continuously dropping apparatus and an apparatus to concentrate an azeotropic vapor of epichlorohydrin and water under reduced pressure and to return only epichlorohydrin to the reaction system, 774 g (6 mols) of cyanuric acid, 8,328 g (90 mols) of epichlorohydrin and 213 g of a tetramethylammonium chloride aqueous solution having a concentration of 15.5 wt %, were added and refluxed with stirring at from 89 to 120° C. for 5 hours to carry out the reaction. Then, the temperature of the reaction system was cooled to 50° C., and 1,536 g of a 50 wt % sodium hydroxide aqueous solution was added and reacted for 6 hours under a reduced pressure of from 100 to 60 Torr with stirring while maintaining the temperature at 50° C. for dehydrochlorination. Then, formed sodium chloride was dissolved by an addition of 3,600 g of water for washing, followed by liquid separation, and 1,200 g of a 5 wt % sodium dihydrogen phosphate aqueous solution was further added for washing, whereby sodium hydroxide used in an excess amount was neutralized, followed by washing with 4,800 g of water.

Step (B): To 1,600 g of tris-(2,3-epoxypropyl)-isocyanurate obtained by evaporating the reaction solution to dryness at 120° C. under 2 Torr, 1,600 g of dioxane was added.

Step (C"): The temperature was raised to 75° C. to completely dissolve the solid content, then the liquid was cooled to 65° C. over one hour, whereupon 11.2 g of β-form tris-(2,3-epoxypropyl)-isocyanurate having an average particle size of 45 μm was added as seed crystals (the number T of seed crystals was 1×10$^5$ particles/g).

The liquid was stirred at 75° C. for 1 hour and then cooled to 30° C. over 4 hours to precipitate β-form tris-(2,3-epoxypropyl)-isocyanurate crystals, which were collected by filtration.

Step (D): The obtained crystals were washed with 600 g of methanol, followed by filtration.

The obtained cake was dried at 80° C. under a reduced pressure of 5 Torr for 4 hours to obtain β-form tris-(2,3-epoxypropyl)-isocyanurate crystals in a yield of 296 g. The obtained crystals had amounts of remaining dioxane and epichlorohydrin of 1,000 ppm and 40 ppm, respectively, an epoxy equivalent of 101 g/eq., an amount of hydrolyzable chlorine of 150 ppm, an amount of α-form tris-(2,3-epoxypropyl)-isocyanurate extractable by methanol of 0.5 wt % and a content of α-form tris-(2,3-epoxypropyl)-isocyanurate not extractable by methanol contained in the interior of the crystals of 7.0 wt %. The crystals had a melting point of from 150 to 156° C., an average particle size of 70 μm, and they were white crystals. Further, the crystals were dried in a nitrogen stream at 130° C. under a reduced pressure of 10 Torr by a rotary evaporator for 24 hours to obtain β-form tris-(2,3-epoxypropyl)-isocyanurate crystals wherein the amounts of remaining dioxane and epichlorohydrin were 120 ppm and 20 ppm, respectively

EXAMPLE 6

Step (A): Into a flask equipped with a stirrer, a thermometer, a continuously dropping apparatus and an apparatus to concentrate an azeotropic vapor of epichlorohydrin and water under reduced pressure and to return only epichlorohydrin to the reaction system, 774 g (6 mols) of cyanuric acid, 8,328 g (90 mols) of epichlorohydrin and 213 g of a tetramethylammonium chloride aqueous solution having a concentration of 15.5 wt %, were added and refluxed with stirring at from 89 to 120° C. for 5 hours to carry out the reaction. Then, the temperature of the reaction system was cooled to 50° C., and 1,536 g of a 50 wt % sodium hydroxide aqueous solution was added and reacted for 6 hours under a reduced pressure of from 100 to 60 Torr with stirring while maintaining the temperature at 50° C. for dehydrochlorination. Then, formed sodium chloride was dissolved by an addition of 3,600 g of water for washing, followed by liquid separation, and 1,200 g of a 5 wt % sodium dihydrogen phosphate aqueous solution was further added for washing, whereby sodium hydroxide used in an excess amount was neutralized, followed by washing with 4,800 g of water.

Step (B): To 1,600 g of tris-(2,3-epoxypropyl)-isocyanurate obtained by evaporating the reaction solution to dryness at 120° C. under 2 Torr, 1,600 g of acetonitrile was added.

Step (C): The temperature was raised to 75° C. to completely dissolve the solid content, then the liquid was cooled to 14° C. over 7 hours to precipitate β-form tris-(2,3-epoxypropyl)-isocyanurate crystals, which were collected by filtration.

Step (D): The obtained crystals were washed with 600 g of methanol, followed by filtration.

The obtained cake was dried at 80° C. under a reduced pressure of 5 Torr for 4 hours to obtain β-form tris-(2,3-epoxypropyl)-isocyanurate crystals in a yield of 288 g. The obtained crystals had amounts of remaining acetonitrile and epichlorohydrin of 1,000 ppm and 60 ppm, respectively, an epoxy equivalent of 102 g/eq., an amount of hydrolyzable chlorine of 240 ppm, a content of α-form tris-(2,3-epoxypropyl)-isocyanurate extractable by methanol of 0.5 wt % and a content of α-form tris-(2,3-epoxypropyl)-isocyanurate not extractable by methanol contained in the interior of the crystals of 9.0 wt %. The crystals had a melting point of from 149 to 156° C., an average particle size of 60 μm, and they were white crystals. Further, the crystals were dried in a nitrogen stream at 130° C. under a reduced pressure of 10 Torr by a rotary evaporator for 24 hours to obtain β-form tris-(2,3-epoxypropyl)-isocyanurate crystals wherein the amounts of remaining acetonitrile and epichlorohydrin were 220 ppm and 40 ppm, respectively.

In the present invention, epichlorohydrin in the reaction solution is once replaced by a predetermined solvent after distillation, and then recrystallization is carried out. Accordingly, there is substantially no influence by hydrolyzable chlorine such as epichlorohydrin. Further, the remaining solvent for recrystallization can be reduced.

The filtrate obtained by subjecting the reaction solution to filtration after crystallization, contains a high concentration of α-form tris-(2,3-epoxypropyl)-isocyanurate. For the purpose of producing tris-(2,3-epoxypropyl)-isocyanurate for application in which ratio change of the α-form and the β-form is acceptable, it is possible to return the filtrate to step (A) in production batch. Further, most of epichlorohydrin in the filtrate may be recovered by distillation, and a mixed liquid of α-form tris-(2,3-epoxypropyl)-isocyanurate and epichlorohydrin as evaporation tank bottom may be subjected to waste disposal by means of e.g. incineration. In a case of waste disposal, if epichlorohydrin is distilled off too much, the entire tank bottom may be solidified at room temperature and its handling tends to be difficult, and accordingly epichlorohydrin has to be remained usually in such an amount that the entire tank bottom is liquid or it may be slurried at room temperature.

However, one containing a large amount of chlorine compounds is not preferred in view of corrosion of equipments and generation of dioxin during incineration treatment. When epichlorohydrin is distilled off before crystallization as in the present invention, a tank bottom liquid or slurry containing substantially no chlorine can be obtained, whereby incineration can be carried out easily.

The entire disclosure of Japanese Patent Application No. 2000-311505 filed on Oct. 12, 2000 including specification, claims and summary are incorporated herein by reference in its entirety.

What is claimed is:

1. A process for producing β-form tris-(2,3-epoxypropyl)-isocyanurate crystals containing from 2 to 15 wt % of α-form tris-(2,3-epoxypropyl)-isocyanurate in the interior of the crystals, comprising:

(A) reacting cyanuric acid with epichlorohydrin to form an addition product of cyanuric acid and epichlorohydrin, and dehydrochlorinating said product to obtain a reaction solution containing tris-(2,3-epoxypropyl)-isocyanurate, (B) removing epichlorohydrin from said reaction solution, and dissolving tris-(2,3-epoxypropyl)-isocyanurate in an organic solvent, wherein said solvent is acetonitrile, toluene, dioxane or dimethylformamide, to form a solution, (C) gradually cooling the solution of (B) at a cooling rate of at most 20° C./hr for crystallization, and filtering to obtain crystals, and (D) washing and drying said crystals, wherein said crystals have a remaining epichlorohydrin content of at most 100 ppm.

2. The process according to claim 1, wherein (A) comprises reacting: (a) 1 mol of cyanuric acid, (b) from 5 to 180 mols of epichlorohydrin and (c) a catalyst of from 0.001 to 0.1 mol of at least one compound selected from the group consisting of a tertiary amine, a quaternary ammonium salt, a quaternary ammonium base, a tri-substituted phosphine and a quaternary phosphonium salt, to obtain said reaction solution, and adding from 2 to 6 mols of an alkali metal hydroxide or an alkali metal alcoholate to said reaction solution for dehydrochlorination, and removing the resulting alkali metal salt to obtain said reaction solution containing tris-(2,3-epoxypropyl)-isocyanurate.

3. The process according to claim 1, wherein ultrasonic waves are applied to said solution of (B), when gradually cooling said solution in (C).

4. The process according to claim 1, wherein said washing in (D) is carried out by using a solvent capable of providing a solubility of at least 0.5 g/100 g, at 20° C., to α form tris-(2,3-epoxypropyl)-isocyanurate and a solubility of less than 0.5 g/100 g, at 20° C., to β form tris-(2,3-epoxypropyl)-isocyanurate, in an amount of from 0.5 to 10 times by weight relative to the β form tris-(2,3-epoxypropyl)-isocyanurate crystals.

5. The process according to claim 1, wherein the average particle size of said crystals obtained in (C) is from 20 to 500 μm, and said drying in (D) is carried out under atmospheric pressure or under reduced pressure in a gas stream at a temperature of from 120 to 140° C.

6. The process according to claim 1, wherein the average particle size of said crystals obtained in (C) is from 10 to 20 μm, and said drying in (D) is carried out under atmospheric pressure or under reduced pressure in a gas stream at a temperature of from 40 to 120° C.

7. A process for producing β-form tris-(2,3-epoxypropyl)-isocyanurate crystals containing from 2 to 15 wt % of α-form tris-(2,3-epoxypropyl)-isocyanurate in the interior of the crystals, comprising:

(A) reacting cyanuric acid with epichlorohydrin to form an addition product of cyanuric acid and epichlorohydrin, and dehydrochlorinating said product to obtain a reaction solution containing tris-(2,3-epoxypropyl)-isocyanurate, (B) removing epichlorohydrin from said reaction solution, and dissolving tris-(2,3-epoxypropyl)-isocyanurate in an organic solvent, wherein said solvent is acetonitrile, toluene, dioxane or dimethylformamide, to form a solution (C') adding seed crystals to the solution of (B) at a temperature from 5 to 20° C. lower than the temperature at which said solution forms a saturated solution, and gradually cooling said solution at a cooling rate of at most 20° C./hr for crystallization, and filtering to obtain crystals, and (D) washing and drying said crystals, wherein said crystals have a remaining epichlorohydrin content of at most 100 ppm.

8. The process according to claim 7, wherein (A) comprises reacting: (a) 1 mol of cyanuric acid, (b) from 5 to 180 mols of epichlorohydrin and (c) a catalyst of from 0.001 to 0.1 mol of at least one compound selected from the group consisting of a tertiary amine, a quaternary ammonium salt, a quaternary ammonium base, a tri-substituted phosphine and a quaternary phosphonium salt, to obtain a reaction solution, and adding from 2 to 6 mols of an alkali metal hydroxide or an alkali metal alcoholate to said reaction solution for dehydrochlorination, and removing the resulting alkali metal salt to obtain said reaction solution containing tris-(2,3-epoxypropyl)-isocyanurate.

9. The process according to claim 7, wherein said addition of said seed crystals in (C') satisfies the following formulae (1) and (2):

$$1 \times 10^{10} \geq T \geq 1 \times 10^2 \quad (1)$$

$$T = 1.4 \times 10^{12} (m/(M \times D^3)) \quad (2)$$

wherein T is the number of said seed crystals added per the weight of tris-(2,3-epoxypropyl)-isocyanurate in said reaction solution (number/g), m is the weight (g) of said seed crystals added, D is the average particle size of said seed crystals which is from 2 to 300 μm, and M is the weight (g) of tris-(2,3-epoxypropyl)-isocyanurate in the reaction solution.

10. The process according to claim 7, wherein said seed crystals added in (C') are β form tris-(2,3-epoxypropyl)-isocyanurate crystals, or a mixture of β form tris-(2,3-epoxypropyl)-isocyanurate crystals and α form tris-(2,3-epoxypropyl)-isocyanurate crystals.

11. The process according to claim 7, wherein ultrasonic waves are applied to said solution of (B), when gradually cooling said solution in (C').

12. The process according to claim 7, wherein said washing in (D) is carried out by using a solvent capable of providing a solubility of at least 0.5 g/100 g, at 20° C., to α form tris-(2,3-epoxypropyl)-isocyanurate and a solubility of less than 0.5 g/100 g, at 20° C., to β form tris-(2,3-epoxypropyl)-isocyanurate, in an amount of from 0.5 to 10 times by weight relative to the β form tris-(2,3-epoxypropyl)-isocyanurate crystals.

13. The process according to claim 7, wherein the average particle size of said crystals obtained in (C') is from 20 to 500 μm, and said drying in (D) is carried out under atmospheric pressure or under reduced pressure in a gas stream at a temperature of from 120 to 140° C.

14. The process according to claim 7, wherein the average particle size of said crystals obtained in (C') is from 10 to 20 μm, and said drying in (D) is carried out under atmospheric pressure or under reduced pressure in a gas stream at a temperature of from 40 to 120° C.

15. A process for producing β form tris-(2,3-epoxypropyl)-isocyanurate crystals containing from 2 to 15 wt % of α-form tris-(2,3-epoxypropyl)-isocyanurate in the interior of the crystals, comprising:

(A) reacting cyanuric acid with epichlorohydrin to form an addition product of cyanuric acid and epichlorohydrin, and dehydrochlorinating said product to obtain a reaction solution containing tris-(2,3-epoxypropyl)-isocyanurate, (B) removing epichlorohydrin from said reaction solution, and dissolving tris-(2,3-epoxypropyl)-isocyanurate in a solvent, wherein said solvent is acetonitrile, toluene, dioxane or dimethylformamide, to form a solution, (C″) heating the solution of (B) to a temperature of at least the temperature at which said solution forms a saturated solution, thereafter cooling said solution to a temperature from 5 to 20° C. lower than the temperature at which said solution forms a saturated solution, and adding seed crystals thereto, and then gradually cooling said solution at a cooling rate of at most 20° C./hr for crystallization and filtering to obtain crystals, and (D) washing and drying said crystals, wherein said crystals have a remaining epichlorohydrin content of at most 100 ppm.

16. The process according to claim 15, wherein (A) comprises reacting: (a) 1 mol of cyanuric acid, (b) from 5 to 180 mols of epichlorohydrin and (c) a catalyst of from 0.001 to 0.1 mol of at least one compound selected from the group consisting of a tertiary amine, a quaternary ammonium salt, a quaternary ammonium base, a tri-substituted phosphine and a quaternary phosphonium salt, to obtain a reaction solution, and adding from 2 to 6 mols of an alkali metal hydroxide or an alkali metal alcoholate to said reaction solution for dehydrochlorination, and then removing the resulting alkali metal salt to obtain said reaction solution containing tris-(2,3-epoxypropyl)-isocyanurate.

17. The process according to claim 15, wherein said addition of said seed crystals in (C″) satisfies the following formulae (1) and (2):

$$1 \times 10^{10} \geq T \geq 1 \times 10^2 \quad (1)$$

$$T = 1.4 \times 10^{12} (m/(M \times D^3)) \quad (2)$$

wherein T is the number of said seed crystals added per the weight of tris-(2,3-epoxypropyl)-isocyanurate in said reaction solution (number/g), m is the weight (g) of said seed crystals added, D is the average particle size of seed crystals which is from 2 to 300 μm, and M is the weight (g) of tris-(2,3-epoxypropyl)-isocyanurate in the reaction solution.

18. The process according to claim 15, wherein said seed crystals added in (C″) are β form tris-(2,3-epoxypropyl)-isocyanurate crystals, or a mixture of β form tris-(2,3-epoxypropyl)-isocyanurate crystals and α-form tris-(2,3-epoxypropyl)-isocyanurate crystals.

19. The process according to claim 15, wherein ultrasonic waves are applied to said solution of (B), in the process of gradually cooling said solution in (C″).

20. The process according to claim 15, wherein said washing in (D) is carried out by using a solvent capable of providing a solubility of at least 0.5 g/100 g, at 20° C., to α-form tris-(2,3-epoxypropyl)-isocyanurate and a solubility of less than 0.5 g/100 g, at 20° C. to β form tris-(2,3- epoxypropyl)-isocyanurate, in an amount of from 0.5 to 10 times by weight relative to the β form tris-(2,3-epoxypropyl)-isocyanurate crystals.

21. The process according to claim 15, wherein the average particle size of said crystals obtained in (C") is from 20 to 500 μm, and said drying in (D) is carried out under atmospheric pressure or under reduced pressure in a gas stream at a temperature of from 120 to 140° C.

22. The process according to claim 15, wherein the average particle size of said crystals obtained in (C") is from 10 to 20 μm, and said drying in (D) is carried out under atmospheric pressure or under reduced pressure in a gas stream at a temperature of from 40 to 120° C.

23. The process according to claim 1, wherein said removing epichlorohydrin is carried out by coating a film of said reaction solution on a substrate and heating.

24. The process according to claim 23, wherein said heating is from 100 to 165° C.

25. The process according to claim 23, wherein said removing epichlorohydrin is carried out under reduced pressure.

26. The process according to claim 23, wherein said film has a thickness of from 30 to 500 micron.

27. The process according to claim 7, wherein said removing epichlorohydrin is carried out by coating a film of said reaction solution on a substrate and heating.

28. The process according to claim 27, wherein said heating is from 100 to 165° C.

29. The process according to claim 27, wherein said removing epichlorohydrin is carried out under reduced pressure.

30. The process according to claim 27, wherein said film has a thickness of from 30 to 500 micron.

31. The process according to claim 15, wherein said removing epichlorohydrin is carried out by coating a film of said reaction solution on a substrate and heating.

32. The process according to claim 31, wherein said heating is from 100 to 165° C.

33. The process according to claim 31, wherein said removing epichlorohydrin is carried out under reduced pressure.

34. The process according to claim 31, wherein said film has a thickness of from 30 to 500 micron.

35. The process according to claim 1, wherein in step (B), the tris-(2,3-epoxypropyl)-isocyanurate is dissolved in acetonitrile, dioxane or dimethylformamide.

36. The process according to claim 7, wherein in step (B), the tris-(2,3-epoxypropyl)-isocyanurate is dissolved in acetonitrile, dioxane or dimethylformamide.

37. The process according to claim 15, wherein in step (B), the tris-(2,3-epoxypropyl)-isocyanurate is dissolved in acetonitrile, dioxane or dimethylformamide.

* * * * *